(12) United States Patent
Kawamura et al.

(10) Patent No.: US 10,584,084 B2
(45) Date of Patent: Mar. 10, 2020

(54) PROCESS FOR PRODUCING 2,3-BUTANEDIOL

(71) Applicant: Toray Industries, Inc., Tokyo (JP)

(72) Inventors: Kenji Kawamura, Kamakura (JP); Izumi Morita, Tokai (JP); Masateru Ito, Kamakura (JP); Kyohei Isobe, Kamakura (JP); Satoshi Sakami, Kamakura (JP); Katsushige Yamada, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 788 days.

(21) Appl. No.: 14/350,366

(22) PCT Filed: Oct. 12, 2012

(86) PCT No.: PCT/JP2012/076421
§ 371 (c)(1),
(2) Date: Apr. 8, 2014

(87) PCT Pub. No.: WO2013/054874
PCT Pub. Date: Apr. 18, 2013

(65) Prior Publication Data
US 2014/0238841 A1 Aug. 28, 2014

(30) Foreign Application Priority Data
Oct. 14, 2011 (JP) .................... 2011-226391

(51) Int. Cl.
*C07C 29/76* (2006.01)
*C07C 29/80* (2006.01)
(Continued)

(52) U.S. Cl.
CPC .............. *C07C 29/80* (2013.01); *C07C 29/76* (2013.01); *C12P 7/16* (2013.01); *C12P 7/18* (2013.01);
(Continued)

(58) Field of Classification Search
CPC ........ C07C 29/76; C07C 29/80; C07C 31/207; B01D 59/30
(Continued)

(56) References Cited

U.S. PATENT DOCUMENTS 4,479,021 A 10/1984 Issler et al.
6,117,277 A 9/2000 Zgorzelski et al.
(Continued)

FOREIGN PATENT DOCUMENTS

CN 101586126 A 11/2009
JP 60-78928 A 5/1985
(Continued)

OTHER PUBLICATIONS

English Translation of JP 2004-352731 (application No. 2004-137356) obtained from AIPN.*
(Continued)

*Primary Examiner* — Jonathan Luke Pilcher
(74) *Attorney, Agent, or Firm* — DLA Piper LLP (US)

(57) ABSTRACT

A method of producing 2,3-butanediol includes subjecting a 2,3-butanediol culture liquid produced by microbial fermentation to nanofiltration membrane treatment and ion-exchange treatment (Step A), and then adding an alkaline substance and performing distillation (Step B).

11 Claims, 1 Drawing Sheet (51) Int. Cl.
  *B01D 59/30* (2006.01)
  *C07C 31/20* (2006.01)
  *C12P 7/18* (2006.01)
  *C12P 7/16* (2006.01)
(52) U.S. Cl.
  CPC ............ *B01D 59/30* (2013.01); *C07C 31/207* (2013.01); *Y02E 50/10* (2013.01)
(58) Field of Classification Search
  USPC ........................................................ 568/868
  See application file for complete search history.

(56) References Cited

U.S. PATENT DOCUMENTS

| | | | |
|---|---|---|---|
| 6,361,983 B1 | 3/2002 | Ames | |
| 7,919,658 B2* | 4/2011 | Adkesson | B01D 61/027 568/868 |
| 8,183,417 B2* | 5/2012 | Adkesson | B01D 61/027 568/868 |
| 8,399,717 B2* | 3/2013 | Rousseaux | B01D 11/0415 568/868 |
| 8,597,918 B2* | 12/2013 | Clark | C07C 29/76 435/132 |
| 9,018,424 B2* | 4/2015 | Morita | C07C 29/76 568/868 |
| 9,499,460 B2* | 11/2016 | Kawamura | C07C 29/76 |
| 2005/0069997 A1* | 3/2005 | Adkesson | B01D 61/027 435/158 |
| 2011/0003355 A1 | 1/2011 | Clark et al. | |
| 2011/0152581 A1* | 6/2011 | Adkesson | B01D 61/027 568/852 |
| 2011/0152583 A1* | 6/2011 | Adkesson | B01D 61/027 568/872 |
| 2011/0257441 A1* | 10/2011 | Rousseaux | B01D 11/0415 568/872 |
| 2012/0253082 A1* | 10/2012 | Morita | C07C 29/76 568/869 |
| 2016/0052845 A1* | 2/2016 | Kawamura | C07C 29/80 528/308.8 |
| 2016/0185694 A1* | 6/2016 | Kawamura | C07C 29/76 568/872 |
| 2016/0298144 A1* | 10/2016 | Isobe | C12P 7/18 |

FOREIGN PATENT DOCUMENTS

| | | |
|---|---|---|
| JP | 11-500437 A | 1/1999 |
| JP | 2001-213828 A | 8/2001 |
| JP | 2004-352713 A | 12/2004 |
| JP | 2006-502202 A | 1/2006 |
| JP | 2007-502325 A | 2/2007 |
| JP | 2010-150248 A | 7/2010 |
| WO | 2007/094178 A1 | 8/2007 |
| WO | 2009/151342 A1 | 12/2009 |

OTHER PUBLICATIONS

English Translation of JP 2010-150248 (application No. 2009-269014) obtained from AIPN.*
Matsuo, Y. et al., "Determination of Residual Glucose, Hydroxymethylfurfural and Oligosaccharides in Acid-Hydrolyzates of Glucose," *Journal of Fermentation Technology*, 1961, No, 39, vol. 5, pp. 256-262, with English Abstract.
Supplementary European Search Report dated Jun. 3, 2015 of corresponding European Application No. 12839561.3.
Jianying, D. et al., "Research Progress of Bio-Based Chemical 2,3-Butandiol," *The Chinese Journal of Process Engineering*, 2010, vol. 10, No. 1, pp. 200-208 along with a partial English translation.
Donald F. Othmer et al., "Pryolysis of 2,3-Butylene Glycol Diacetate to Butadiene," Ind. Eng. Chem., 1945, vol. 37, No. 9, pp. 905-908 (first page).
A.N. Bourns et al., "The Catalytic Action of Aluminium Silicates: 1. The Dehydration of Butanediol-2,3 and Butanone-2 Over Activated Morden Bentonite," Canadian Journal of Research, 1947, vol. 25b, No. 1, pp. 80-89 (abstract).
"Microbial production of meso-2,3-butanediol by metabolically engineered *Escherichia coli* under low oxygen condition," Applied Microbiology and Biotechnology, Aug. 2010, vol. 87, Issue 6, pp. 2001-2009 (abstract).

* cited by examiner

PROCESS FOR PRODUCING 2,3-BUTANEDIOL

TECHNICAL FIELD

This disclosure relates to a method of obtaining highly pure 2,3-butanediol exhibiting no pigmentation from a 2,3-butanediol fermentation liquid by a simple method.

BACKGROUND 2,3-Butanediol (BDO) is a useful compound having 3 types of optical isomers, and is used as an intermediate material for pharmaceuticals and cosmetics; and as a material for inks, perfumes, liquid crystals, insecticides, softening agents, explosives, plasticizers and the like. Industrially, it is produced by a method in which 2-butene oxide is hydrolyzed in an aqueous perchloric acid solution. On the other hand, in recent years, to solve the problems of depletion of petroleum resources and global warming, achievement of a sustainable, recycling-oriented society is demanded. Also, in the chemical industry, shifting from petroleum materials to biomass-derived materials is being intensively studied. In particular, microbial fermentation of 2,3-butanediol is attracting attention. It has been reported that 2,3-butanediol is converted to methyl ethyl ketone, which is a general-purpose solvent, by chemical conversion (A. N. Bourns, The Catalytic Action of Aluminium Silicates, Canadian J. Res. (1947)), and that 2,3-butanediol is converted to 1,3-butadiene by acetylation followed by elimination of acetic acid (Nathan Shlechter, Pyrolysis of 2,3-butylene Glycol Diacetate to Butadiene, Indu. Eng. Chem. 905 (1945)). In particular, production techniques for 1,3-butadiene are very important since 1,3-butadiene is a starting substance that enables synthesis of many kinds of compounds such as hexamethylenediamine, adipic acid and 1,4-butanediol, and establishment of those techniques might replace the existing petroleum-derived synthetic resins with biomass-derived resins.

Examples of generally known microorganisms that produce 2,3-butanediol include *Klebsiella Pneumoniae*, *Klebsiella axytoca* and *Paenibacillus polymyxa*, and 2,3-butanediol is produced by fermentation production by these microorganisms. However, fermentation liquids contain not only 2,3-butanediol, but also various impurities such as residual medium components and metabolic by-products of the microorganisms. In particular, sugars as nutrient sources for the microorganisms; organic acids and proteins as their metabolic products and the like are reported to generate colored impurities by heat (Yoshiyuki Matsuo, Mode of Overdecomposition of Glucose by Acid: Journal of Fermentation Technology 39, 5, 256-262 (1961)). Therefore, application of the fermentation liquid to the above-described uses require high-level purification of 2,3-butanediol.

As a method of purifying 2,3-butanediol, JP 2010-150248 A discloses a purification method in which a diol such as 2,3-butanediol is purified by combination of nanofiltration membrane treatment and distillation. As another method for purifying a diol, U.S. Pat. No. 6,361,983 B discloses a method in which the pH of a 1,3-propanediol fermentation liquid is adjusted to not less than 7 and the resulting fermentation liquid is then subjected to a separation step, to reduce coloration of 1,3-propanediol. As a method of producing a highly pure diol, Japanese Translated PCT Patent Application Laid-open No. 2007-502325 discloses a method of producing 1,3-propanediol by microfiltration, ultrafiltration, nanofiltration, ion exchange, distillation and then hydrogenation reduction treatment.

In the above-described method of purifying 2,3-butanediol, that is, in the purification of a 2,3-butanediol fermentation liquid by nanofiltration membrane treatment followed by distillation, highly pure 2,3-butanediol can be obtained, but there still remains a problem that the distillation step causes remarkable coloration of the 2,3-butanediol. In view of this, it could be helpful to provide a method of purifying a 2,3-butanediol fermentation liquid by distillation, wherein 2,3-butanediol is separated/recovered while coloration of 2,3-butanediol is prevented.

SUMMARY

We discovered that, by subjecting a 2,3-butanediol fermentation liquid to nanofiltration membrane treatment and ion-exchange treatment and then adding an alkaline substance and performing distillation, 2,3-butanediol having a high purity and remarkably low degree of pigmentation can be obtained.

We thus provide:

(1) A method of producing 2,3-butanediol, the method comprising the steps of: subjecting a 2,3-butanediol culture liquid produced by microbial fermentation to nanofiltration membrane treatment and ion-exchange treatment (Step A), and then adding an alkaline substance and performing distillation (Step B).

(2) The method of producing 2,3-butanediol according to (1), wherein the amount of the alkaline substance added is not more than 10 mol % with respect to the amount (number of moles) of 2,3-butanediol.

(3) The method of producing 2,3-butanediol according to (1) or (2), wherein the alkaline substance is at least one selected from the group consisting of alkali metal hydroxides, alkaline earth metal hydroxides, alkali metal carbonates, alkali metal hydrogen carbonates and alkaline earth metal carbonates.

(4) The method of producing 2,3-butanediol according to any one of (1) to (3), wherein the alkaline substance is at least one selected from the group consisting of sodium hydroxide, potassium hydroxide, calcium hydroxide, magnesium hydroxide, sodium carbonate and calcium carbonate.

(5) The method of producing 2,3-butanediol according to any one of (1) to (4), further comprising concentrating, before the Step B, the 2,3-butanediol solution obtained in the Step A (Step C).

(6) The method of producing 2,3-butanediol according to (5), wherein the Step C is a step of filtering a 2,3-butanediol solution through a reverse osmosis membrane.

In a method of producing 2,3-butanediol by microbial fermentation, highly pure and colorless 2,3-butanediol can be obtained by a much simpler method than in the prior art.

DESCRIPTION OF SYMBOLS

1. Supply tank
2. Nanofiltration membrane element
3. High-pressure pump
4. Flow of permeate from nanofiltration membrane 5. Flow of non-permeate of nanofiltration membrane
6. Flow of supply liquid for nanofiltration membrane

DETAILED DESCRIPTION 2,3-Butanediol Culture Liquid

Our methods are characterized in that 2,3-butanediol is produced by microbial fermentation. In terms of microorganisms that use sugars as carbon sources for fermentation, *Klebsiella pneumoniae, Klebsiella oxymora* and *Paenibacillus polymyxa* are present in the natural environment and are capable of producing (2R,3R)-threo isomers and (2S, 3R)-meso isomers. Further, the genus *Ochribactrum* as shown in WO2007/094178 is known to selectively produce (2S,3S,)-threo isomers. Further, as a microorganism that is capable of fermentation using carbon monoxide as a carbon source, *Clostridium autoethanogenum* is known as described in WO2009/151342, and 2,3-butanediol produced from such a microorganism can also be a subject of our methods.

Alternatively, the method may be a method using a microorganism that was given a 2,3-butanediol-producing capacity by genetic recombination, and specific examples of such a method include the method described in Applied Microbiology and Biotechnology, Volume 87, Number 6, 2001-2009 (2010).

As described above, 2,3-butanediol produced by microbial fermentation has three types of optical isomers. The subject of production may be any one of the isomers, or may be a mixture of a plurality of the isomers. Since each isomer may produce a by-product depending on its use, the 2,3-butanediol preferably has high optical activity. 2,3-Butanediol having high optical activity can be obtained by using, as described above, a microorganism that produces 2,3-butanediol having high optical activity.

The culture liquid means a liquid obtained as a result of growth of a microorganism or cultured cells in a fermentation feedstock. The composition of the fermentation feedstock added to the culture liquid may be appropriately changed from the fermentation feedstock composition used in the beginning of the culture such that the productivity of the 2,3-butanediol of interest increases.

Examples of the carbon source in the fermentation feedstock include sugars such as glucose, fructose, sucrose, xylose, arabinose, galactose, mannose and starch. Further, the sugars may be commercially available purified products; degraded products of recycled resources or biomasses; or degraded products of cellulose, hemicellulose or lignin materials, prepared by chemical or biological treatment. In such cases, impurities that inhibit fermentative production by microorganisms are preferably reduced by purification. Further, when the above-described *Clostridium autoethanogenum* is used, carbon monoxide may be a carbon source. Carbon monoxide can be obtained by incomplete combustion of coal, petroleum or a biomass resource; can be recovered from the gas generated from a coke oven or the like in an ironworks; or can be produced by gasification of a biomass resource.

Preferred examples of the nitrogen source in the fermentation feedstock include ammonia gas, aqueous ammonia, ammonium salts, urea and nitrates, which are low-cost inorganic nitrogen sources; and oil cakes, soybean hydrolysates, casein digests, meat extracts, yeast extracts, peptone, amino acids and vitamins, which are organic nitrogen sources.

Examples of inorganic salts which may be added as appropriate to the fermentation feedstock include phosphates, magnesium salts, calcium salts, iron salts and manganese salts. Where the microorganism requires a specific nutrient (e.g., amino acid) for its growth, the nutrient itself or a natural product containing it may be added. An anti-forming agent may also be used as required.

Culture conditions for production of 2,3-butanediol may be selected such that the conditions are optimum for the microorganism used. For example, in terms of the aeration condition during the culture, the culture may be either aerobic culture or anaerobic culture. To increase productivity of the 2,3-butanediol, microaerobic culture is preferred. The pH during the culture is preferably within the range of 4 to 8. The pH of the culture liquid is adjusted to a pre-determined value within the above-described range using an alkaline substance and acidic substance. Preferred examples of the basic substance used include calcium hydroxide, calcium carbonate, sodium hydroxide, potassium hydroxide, ammonia gas and aqueous ammonia. Preferred examples of the acidic substance used include sulfuric acid, hydrochloric acid, acetic acid, carbon dioxide gas and carbonated water. The culture temperature is preferably 20 to 40° C.

The method of culturing a microorganism is not limited as long as it is a method known to those skilled in the art, and may be either batch culture or continuous culture. In view of productivity, continuous culture is preferred since it is carried out while fresh cells capable of fermentation production are grown. For example, in terms of the method of continuous culture, batch culture or fed-batch culture may be carried out at the initial phase of the culture to increase the microbial concentration, followed by starting continuous culture (withdrawal), or the cells may be inoculated at a high concentration and continuous culture may be carried out from the beginning of the culture. It is possible to start supplying the feedstock medium and withdrawing the culture at appropriate timings. The timing to start supplying the feedstock medium and the timing to start withdrawing the culture are not necessarily the same. Supplying the feedstock medium and withdrawing the culture may be carried out either continuously or intermittently. The nutrients described above required for growth of the cells may be added to the feedstock medium to allow continuous growth of the cells. The concentration of the microorganism or cultured cells in the culture liquid is preferably maintained high within a range which does not cause death of the microorganism or cultured cells at a high rate due to an inappropriate environment of the culture medium for the growth of the microorganism or cultured cells to achieve efficient production. For example, by maintaining the concentration at not less than 5 g/L in terms of dry weight, a good production efficiency can be obtained. The operation of continuous culture is usually preferably carried out in a single fermenter to control the culture. However, the number of fermenters is not restricted as long as the continuous culture is carried out to produce the product while allowing the growth of cells. A plurality of fermenters may be used because of, for example, a small capacity of each fermenter. In this case, high productivity of the fermentation product can be obtained by continuous culture using the plurality of fermenters connected in parallel or in series through pipes.

The composition of the 2,3-butanediol culture liquid subjected to the later nanofiltration membrane treatment and ion-exchange treatment (Step A) is not limited, and sugar(s) and/or inorganic salt(s) used for the fermentation feedstock may be contained therein. Further, even where the culture liquid contains fermentation by-products such as organic acids, amino acids, and/or furan compounds including furfural, high-level purification is possible by our purification method so that the culture liquid can be preferably used.

Step of Nanofiltration Membrane Treatment and Ion-exchange Treatment (Step A)

The later-described step of distillation of 2,3-butanediol (Step B) is preceded by nanofiltration membrane treatment and ion-exchange treatment of the 2,3-butanediol culture liquid (Step A). This is because, where the 2,3-butanediol culture liquid is subjected to distillation without carrying out Step A, a large amount of distillation residue is produced to cause a remarkable decrease in the distillation yield.

As disclosed in JP 2010-150248 A, filtration of a 2,3-butanediol-containing solution through a nanofiltration membrane allows efficient separation of 2,3-butanediol into the permeate side, and inorganic salts, sugars and colored components into the feed side. That is, the nanofiltration membrane treatment means passing a 2,3-butanediol-containing solution through a nanofiltration membrane and recovering the 2,3-butangediol from the permeate side.

Examples of the material of the nanofiltration membrane include polymer materials such as piperazine polyamide, polyamide, cellulose acetate, polyvinyl alcohol, polyimide and polyester; and inorganic materials such as ceramics. A nanofiltration membrane is generally used as a spiral-wound membrane element, or a flat membrane or hollow fiber membrane. The nanofiltration membrane is preferably a spiral-wound membrane element.

Specific examples of the nanofiltration membrane element preferably include "GEsepa", which is a cellulose acetate nanofiltration membrane manufactured by GE Osmonics; NF99 and NF99HF, which are nanofiltration membranes having a functional layer composed of a polyamide, manufactured by Alfa-Laval; NF-45, NF-90, NF-200 and NF-400, which are nanofiltration membranes having a functional layer composed of a cross-linked piperazine polyamide, manufactured by Filmtec Corporation; and SU-210, SU-220, SU-600 and SU-610, which are nanofiltration membrane elements manufactured by Toray Industries, Inc., containing UTC60 manufactured by the same manufacturer. Among these, the nanofiltration membrane element is more preferably NF99 or NF99HF, which are nanofiltration membranes having a functional layer composed of a polyamide, manufactured by Alfa-Laval; NF-45, NF-90, NF-200 or NF-400, which are nanofiltration membranes having a functional layer composed of a cross-linked piperazine polyamide, manufactured by Filmtec Corporation; or SU-210, SU-220, SU-600 or SU-610, which are nanofiltration membrane modules manufactured by Toray Industries, Inc., containing UTC60 manufactured by the same manufacturer. The nanofiltration membrane element is still more preferably SU-210, SU-220, SU-600 or SU-610, which are nanofiltration membrane elements manufactured by Toray Industries, Inc., containing UTC60 manufactured by the same manufacturer, whose major component is a cross-linked piperazine polyamide.

Filtration through a nanofiltration membrane may be carried out under pressure, and the filtration pressure is preferably 0.1 MPa to 8 MPa. Where the filtration pressure is less than 0.1 MPa, the membrane permeation rate may be low, while in cases where the filtration pressure is more than 8 MPa, the membrane may be damaged. Where the membrane is used at a filtration pressure of 0.5 MPa to 7 MPa, the membrane permeation flux is high so that the 2,3-butanediol fermentation liquid can be efficiently allowed to permeate, and the possibility of damaging the membrane is small, which is more preferred. The membrane is especially preferably used at a filtration pressure of 1 MPa to 6 MPa.

The concentration of 2,3-butanediol to be filtered through the nanofiltration membrane is not limited, and the concentration is preferably high since a high 2,3-butanediol concentration in the permeate allows reduction of the energy required for concentration, and the cost can therefore be reduced.

The ion-exchange treatment is a method of removing ionic components from the 2,3-butanediol solution using an ion exchanger. Examples of the ion exchanger include ion-exchange resin, ion-exchange membranes, ion-exchange fibers, ion-exchange papers, gel ion-exchangers, liquid ion-exchangers, zeolite, carbonaceous ion exchangers and montmorillonite. Treatment using an ion-exchange resin is also preferably employed.

Ion-exchange resins are classified depending on their functional groups into strong anion-exchange resins, weak anion-exchange resins, strong cation-exchange resins, weak cation-exchange resins, chelate-exchange resins and the like. Examples of the strong anion-exchange resins include "Amberlite" IRA410J, IRA411 and IRA910CT, manufactured by Organo Corporation; and "DIAION" SA10A, SA12A, SA11A, NSA100, SA20A, SA21A, UBK510L, UBK530, UBK550, UBK535 and UBK555, manufactured by Mitsubishi Chemical Corporation. Examples of the weak anion-exchange resins include "Amberlite" IRA478RF, IRA67, IRA96SB, IRA98 and XE583, manufactured by Organo Corporation; and "DIAION" WA10, WA20, WA21J and WA30, manufactured by Mitsubishi Chemical Corporation. Examples of the strong cation-exchange resins include "Amberlite" IR120B, IR124, 200CT and 252, manufactured by Organo Corporation; and "DIAION" SK104, SK1B, SK110, SK112, PK208, PK212, PK216, PK218, PK220 and PK228, manufactured by Mitsubishi Chemical Corporation. Examples of the weak cation-exchange resins include "Amberlite" FPC3500 and IRC76, manufactured by Organo Corporation; and "DIAION" WK10, WK11, WK100 and WK40L, manufactured by Mitsubishi Chemical Corporation.

Our method is preferably desalination using both an anion-exchange resin(s) and a cation-exchange resin(s), more preferably desalination using a strong anion-exchange resin(s) and a strong cation-exchange resin(s) in view of removing various ions. The anion-exchange resin is regenerated with a dilute aqueous alkaline solution of sodium hydroxide or the like, and used as the OH type. The cation-exchange resin is preferably regenerated with a dilute aqueous acidic solution of hydrochloric acid or the like, and used as the H type. The method of desalination with an ion-exchange resin(s) may be a batch method or column method, and is not limited as long as efficient desalination is possible therewith. A column method is preferably employed since it allows repeated use. The flow rate through the ion-exchange resin is usually controlled based on SV (space velocity), and SV is preferably 2 to 50. SV is more preferably 2 to 10 to achieve higher purity. The ion-exchange resin may be in the form of a gel type such as a porous type, high porous type, MR type or the like that are commercially available, and an ion-exchange resin having an optimum form may be selected depending on the quality of the solution.

The order of the nanofiltration membrane treatment and the ion-exchange treatment in Step A is not limited. Preferably, the 2,3-butanediol culture liquid is subjected to the nanofiltration membrane treatment, and the 2,3-butanediol solution containing reduced inorganic salts obtained from the permeate side is then subjected to the ion-exchange treatment. By this, inorganic salts and organic acids that partially pass through the nanofiltration membrane can be removed by the ion-exchange resin, to increase the removal rate of inorganic salts.

Distillation Step (Step B)

Step A is followed by addition of an alkaline substance and distillation (Step B). By Step B, highly pure/colorless 2,3-butanediol can be obtained.

Preferred examples of the alkaline substance include alkali metal hydroxides such as sodium hydroxide, potassium hydroxide and cesium hydroxide; alkaline earth metal hydroxides such as magnesium hydroxide, calcium hydroxide and barium hydroxide; alkali metal carbonates and alkali metal hydrogen carbonates such as sodium carbonate, sodium hydrogen carbonate, potassium carbonate, potassium hydrogen carbonate and cesium carbonate; alkaline earth metal carbonates such as basic magnesium carbonate and calcium carbonate; and alkali metal carboxylates such as sodium acetate and potassium acetate. Among these, hydroxides, carbonates and hydrogen carbonates of alkali metals; and hydroxides and carbonates of alkaline earth metals; are preferred, and sodium hydroxide, potassium hydroxide, sodium carbonate, potassium carbonate, calcium hydroxide and calcium carbonate are especially preferred in view of the cost and the treatment efficiency. Each of these alkaline substances may be added as it is as a solid, or may be added as an aqueous solution with which the amount of the substance added can be easily controlled. Each of these alkaline substances may be used alone, or a plurality of these may be used.

The amount of the alkaline substance added is not limited. Where the amount of the alkaline substance added is too large, the distillation yield in the distillation may decrease, the amount is preferably not more than 10 mol %, more preferably not more than 5 mol %, still more preferably not more than 3 mol % with respect to the amount (number of moles) of 2,3-butanediol. In batch distillation, the amount of the alkaline substance added may be determined by calculating the number of moles of 2,3-butanediol based on its concentration. The lower limit of the amount of the alkaline substance added is not limited as long as the desired effect is exerted, and the amount is preferably not less than 0.001 mol %, more preferably not less than 0.01 mol %, still more preferably not less than 0.1 mol %.

In continuous distillation, the alkaline substance may be added after calculating the flow of the alkali to be added [mol/h] based on the flow of 2,3-butanediol per unit time [mol/h]. Although the alkaline substance may be continuously fed to the 2,3-butanediol channel, a feeding/mixing tank is preferably provided in view of uniformly adding the substance. U.S. Pat. No. 6,361,983 B and JP 2004-352713 A disclose techniques in which an alkaline substance is added such that the pH of an 1,3-butanediol solution becomes not less than 7 to suppress coloration. However, we discovered that the pH does not contribute to suppression of coloration, and even a pH of not more than 7 can produce the effect.

Upon addition of the alkaline substance, the 2,3-butanediol solution is preferably sufficiently stirred. Although the action of the alkaline substance is still unknown, it is preferred to stir the 2,3-butanediol solution to allow the reaction to proceed sufficiently since the 2,3-butanediol solution is highly viscous. In this process, the solution may be heated since heating has an effect of decreasing the viscosity and promoting the reaction. The temperature is preferably not more than 150° C. to prevent generation of impurities at a high temperature.

Where the alkaline substance is added, it is preferred to concentrate the 2,3-butanediol solution in advance to increase the effect (Step C). The concentration of the concentrated 2,3-butanediol is not limited, and preferably not less than 50 wt % in view of reducing the distillation load. Since a small amount of water is preferably contained for better solubility of the alkaline substance, the concentration is preferably less than 99 wt %.

The method of concentrating the 2,3-butanediol solution may be a general method known to those skilled in the art, and examples of the method preferably applied include methods using a reverse osmosis membrane, concentration under heat using an evaporator, and distillation. A method using a reverse osmosis membrane is preferably applied.

In the method using a reverse osmosis membrane, a 2,3-butanediol solution is filtered through a reverse osmosis membrane to allow water to permeate into the permeate side while 2,3-butanediol is retained and concentrated in the feed side. Examples of the reverse osmosis membrane preferably include composite membranes having a cellulose acetate polymer as a functional layer (hereinafter referred to as cellulose acetate reverse osmosis membranes) and composite membranes having a polyamide functional layer (hereinafter referred to as polyamide reverse osmosis membranes). Examples of the cellulose acetate polymer include polymers prepared with organic acid esters of cellulose such as cellulose acetate, cellulose diacetate, cellulose triacetate, cellulose propionate and cellulose butyrate. Each of these may be used alone, or two or more of these may be used as a mixture or a mixed ester. Examples of the polyamide include linear polymers and cross-linked polymers constituted by aliphatic and/or aromatic diamine monomers. Examples of the form of the membrane that may be used as appropriate include a flat membrane, spiral-wound membrane and hollow fiber membrane.

Specific examples of the reverse osmosis membrane include polyamide reverse osmosis membrane modules manufactured by Toray Industries, Inc. such as low-pressure type modules SU-710, SU-720, SU-720F, SU-710L, SU-720L, SU-720LF, SU-720R, SU-710P and SU-720P, as well as high-pressure type modules SU-810, SU-820, SU-820L and SU-820FA; cellulose acetate reverse osmosis membranes manufactured by the same manufacturer, SC-L100R, SC-L200R, SC-1100, SC-1200, SC-2100, SC-2200, SC-3100, SC-3200, SC-8100 and SC-8200; NTR-759HR, NTR-729HF, NTR-70SWC, ES10-D, ES20-D, ES20-U, ES15-D, ES15-U and LF10-D, manufactured by Nitto Denko Corporation; RO98pHt, R099, HR98PP and CE4040C-30D, manufactured by Alfa-Laval; "GE Sepa" manufactured by GE; and BW30-4040, TW30-4040, XLE-4040, LP-4040, LE-4040, SW30-4040 and SW30HRLE-4040, manufactured by FilmTec Corporation.

The concentration with a reverse osmosis membrane is carried out under pressure. The filtration pressure is preferably 1 MPa to 8 MPa since, where the filtration pressure is less than 1 MPa, the membrane permeation rate may be low, while in cases where the filtration pressure is more than 8 MPa, the membrane may be damaged. In cases where the filtration pressure is 1 MPa to 7 MPa, the membrane permeation flux is high so that the 2,3-butanediol solution can be efficiently concentrated. The filtration pressure is most preferably 2 MPa to 6 MPa in view of reducing the possibility of damaging the membrane. In a 2,3-butanediol solution at a low concentration, a method using a reverse osmosis membrane is preferred in view of the cost.

The method of distillation is not limited and may be simple distillation, precision distillation, atmospheric distillation or distillation under reduced pressure that is generally applied. A thin film distillation apparatus, tray distillation apparatus, packed distillation apparatus or the like may be selected. Either a batch method or continuous method may be used. Distillation under reduced pressure is especially preferred since it can lower the boiling point and, hence, can suppress generation of impurities. More specifically, the heating temperature is preferably 60° C. to 150° C. Where the heating temperature is less than 60° C., an extremely low degree of pressure is required so that maintenance of the apparatus is very difficult at the industrial level. On the other hand, where the heating temperature is more than 150° C., decomposition of sugars and the like remaining in the 2,3-butanediol solution at small amounts occurs, causing by-production of colored substances, which is not preferred. Therefore, the degree of reduction of pressure is preferably controlled such that 2,3-butanediol is distilled within the heating temperature range described above.

Further, to reduce the load on the distillation apparatus, crude distillation may be carried out before the addition of the alkaline substance. The crude distillation is carried out before the main distillation described above. The method of crude distillation is not limited, and simple distillation is generally preferred in view of the cost. By this, the load on the main distillation apparatus can be reduced, and the purity of 2,3-butanediol can be increased. Therefore, the crude distillation may be carried out before adding the alkaline substance and performing the above main distillation.

The purity of 2,3-butanediol produced by our methods is evaluated based on several indices. Examples of indices for the degree of coloration of 2,3-butanediol include Hazen color number (APHA), which enables highly sensitive evaluation of unknown coloration-causing substances. When APHA is not more than 10, coloration can be hardly found by a visual inspection. When the APHA is not more than 5, 2,3-butanediol is even purer and coloration by heating is less likely to occur. The APHA may be measured by a commercially available method defined by JIS K0071-1, or with a commercially available measuring device. Colorless 2,3-butanediol with an APHA of not more than 5 can be obtained.

Examples of methods of measuring impurities other than colored substances include combinations of purity measurement by gas chromatography (GC), purity measurement by UV detection using high performance liquid chromatography (HPLC), and/or the like. Since these are based on evaluation of the ratio of the area of 2,3-butanediol in the total area of detected peaks, a higher ratio means a higher purity of 2,3-butanediol. In purity measurement by measurement of the electric conductivity, a lower electric conductivity means a higher purity of 2,3-butanediol since pure 2,3-butanediol has no electric conductivity.

EXAMPLES

Our methods are described below in more detail by way of Examples, but this disclosure is not limited to the Examples below.

Examples 1 to 3 and Comparative Example 1: Nanofiltration Membrane Treatment and Ion-exchange Treatment Followed by Addition of Alkali and Distillation Preparation of 2,3-Butanediol Fermentation Liquid

*Paenibacillus palymyxa* ATCC12321 was used as the 2,3-butanediol fermentation microorganism. The microorganism was inoculated to 5 mL of the medium shown in Table 1 and cultured with shaking at 30° C. for 24 hours. The resultant was similarly inoculated to 50 mL of the medium shown in Table 1, and preculture was carried out under the same conditions. The resulting preculture was inoculated to 4 L of the medium shown in Table 2, and main culture was performed. The culture was carried out at a temperature of 30° C., aeration rate of 0.5 vvm and stirring rate of 200 rpm, and neutralization was carried out with sodium hydroxide and sulfuric acid such that the pH became 6.5.

TABLE 1

| Component | Concentration |
| --- | --- |
| Glucose | 5 g/L |
| Bactopeptone | 5 g/L |
| Yeast extract | 3 g/L |
| Malt extract | 3 g/L |

TABLE 2

| Component | Concentration |
| --- | --- |
| Glucose | 50 g/L |
| Yeast extract | 13.1 g/L |
| $(NH_4)_2SO_4$ | 5.8 g/L |
| $KH_2PO_4$ | 1.75 g/L |
| $K_2HPO_4$ | 9.2 g/L |
| $(NH_4)_2HPO_4$ | 2.9 g/L |
| $CaCl_2 \cdot 2H_2O$ | 8.8 mg/L |
| $FeSO_4 \cdot 7H_2O$ | 44 mg/L |
| $MnSO_4 \cdot 5H_2O$ | 1.28 mg/L |
| $ZnSO_4 \cdot 7H_2O$ | 0.9 mg/L |
| $MgSO_4 \cdot 7H_2O$ | 219 mg/L |
| EDTA•2Na | 44 mg/L |

The progress of fermentation was judged based on changes in the 2,3-butanediol concentration and glucose concentration. Each concentration was measured under the following HPLC conditions.

Measurement of 2,3-Butanediol Concentration
Column: Shodex Sugar SH1011 (manufactured by Showa Denko K. K.)
Column temperature: 65° C.
Mobile phase: 0.05 M aqueous sulfuric acid solution, 0.6 mL/min.
Detection: RI
Measurement of Glucose Concentration
Column: Asahipak NH2P50 4E (manufactured by Showa Denko K. K.)
Column temperature: 30° C.
Mobile phase: water:acetonitrile=1:3, 0.6 mL/min.
Detection: RI In this study, 2,3-butanediol fermentation reached saturation on Day 3 after the beginning of the culture. The 2,3-butanediol concentration at this time was 16 g/L, and the glucose concentration was 0.9 g/L. The obtained 2,3-butanediol culture liquid was filtered through a microfiltration membrane (manufactured by Toray Industries, Inc.) to remove bacterial cells. This fermentation was repeated 4 times to obtain 16 L of a 2,3-butanediol culture liquid (256 g of 2,3-butanediol).

Purification of 2,3-Butanediol Culture Liquid with Nanofiltration Membrane

Figure 1:
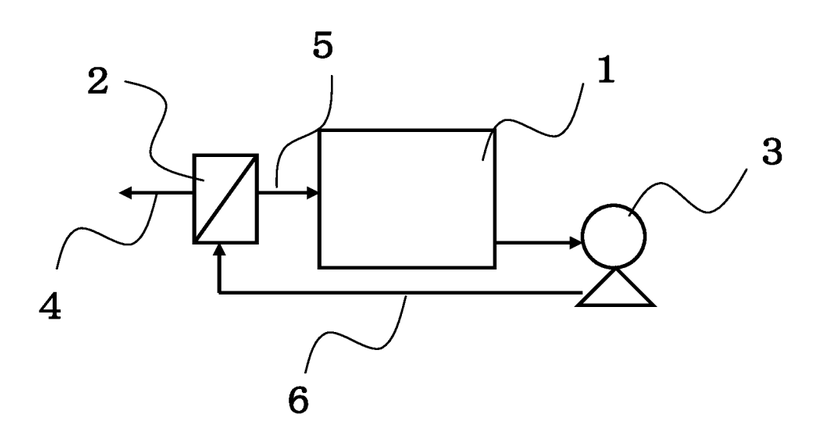
FIG. 1 a schematic diagram illustrating an example of membrane separation apparatus used in our methods.

The culture liquid obtained by the above-described fermentation was purified using the membrane separation apparatus shown in FIG. 1. As the nanofiltration membrane, a spiral-wound membrane element SU-610 (manufactured by Toray Industries, Inc.) was used. The above-described 2,3-butanediol fermentation liquid was fed to a supply tank, and purification by the nanofiltration membrane was carried out by operation at a supply flow rate of 25 L/min., supply liquid pressure of 3 MPa and supply liquid temperature of 20° C. The obtained permeate was a clear 2,3-butanediol solution free from colored components, and most inorganic salt components could be removed, although some components such as potassium ions could not be completely removed. The conditions for measuring ion concentrations by ion chromatography are shown below. The results of this analysis are shown in Table 3.

Measurement of Anion Concentrations
Column: AS4A-SC (manufactured by DIONEX)
Column temperature: 35° C.
Eluent: 1.8 mM sodium carbonate/1.7 mM sodium hydrogen carbonate
Detection: electric conductivity
Measurement of Cation Concentrations
Column: CS12A (manufactured by DIONEX)
Column temperature: 35° C.
Eluent: 20 mM methanesulfonic acid
Detection: electric conductivity

TABLE 3

| | Weight ratio of impurity with respect to 2,3-BDO | |
|---|---|---|
| | Supply liquid for nanofiltration membrane | Permeate from nanofiltration membrane |
| 2,3-BDO | 1.00 | 1.00 |
| Ethanol | 0.35 | 0.30 |
| Lactic acid | 0.41 | 0.10 |
| Formic acid | 0.09 | 0.08 |
| Acetic acid | 0.46 | 0.35 |
| Glucose | 0.06 | 0.00 |
| Phosphate ion | 0.38 | 0.05 |
| Sulfate ion | 0.24 | 0.02 |
| Sodium ion | 0.01 | 0.00 |
| Ammonium ion | 0.10 | 0.10 |
| Potassium ion | 0.29 | 0.07 |

Ion-exchange Purification of 2,3-Butanediol Fermentation Liquid

The permeate obtained by the nanofiltration membrane treatment was subjected to removal of residual ions by ion-exchange treatment. A strong anion-exchange resin IRA120J (manufactured by Organo Corporation) and a strong cation-exchange resin IR410 (manufactured by Organo Corporation) that were regenerated with 1 M sodium hydroxide or 1 M hydrochloric acid into the OH type or H type, respectively, were used. The amount of resin was calculated such that the total amount of inorganic salts and organic acids was the same as the exchange capacity of the ion-exchange resin. Columns were filled with the ion-exchange resins, and the above permeate was passed through the anion-exchange resin and then through the cation-exchange resin at a flow rate SV of 5.

Distillation Purification by Addition of Alkaline Substance

The 2,3-butanediol solution after ion-exchange treatment was subjected to removal of water with a film evaporator MF-10 (manufactured by Tokyo Rikakikai). At this time, water was allowed to evaporate at a degree of reduction of pressure of 30 hPa and a heating temperature of 60° C. To 50 g of the resulting concentrated 2,3-butanediol solution, 0.3 g (1.5 mol % with respect to the amount (number of moles) of 2,3-butanediol; Example 1), 0.7 g (3 mol % with respect to the amount (number of moles) of 2,3-butanediol; Example 2), 2.2 g (10 mol % with respect to the amount (number of moles) of 2,3-butanediol; Example 3) or 4.4 g (20 mol % with respect to the amount (number of moles) of 2,3-butanediol; Example 4) of sodium hydroxide was added, and the resulting mixture was sufficiently stirred until the sodium hydroxide was dissolved. Each resulting solution was distilled under reduced pressure (5 mmHg), to obtain purified 2,3-butanediol. The degree of coloration (APHA), GC purity, distillation yield and electric conductivity of 2,3-butanediol after the distillation were determined by the following measurement methods.

Degree of Coloration (APHA)

The 2,3-butanediol after distillation was diluted 6-fold to prepare 16.67 wt % aqueous solution, and the APHA unit color number was analyzed using a colorimeter (manufactured by Nippon Denshoku Industries Co., Ltd.).

GC Purity

The 2,3-butanediol after distillation was analyzed by gas chromatography (GC; manufactured by Shimadzu Corporation), and the GC purity was calculated according to Equation (1) from the ratio of the peak area of 2,3-butanediol in the total detected peak area.

$$GC\ purity(\%) = 100 \times (2,3\text{-BDO peak area})/(\text{total detected peak area}) \quad (1)$$

The analysis conditions for gas chromatography were as follows:
Column: RT-BDEXM (0.25 mm×30 m, manufactured by Restek)
Column temperature: 75° C.
Vaporizing chamber, detector temperature: 230° C.
Carrier gas: He
Linear velocity: 35 cm/sec.
Detection: flame ionization detector (FID)

Distillation Yield

The distillation yield was calculated according to Equation (2) from the 2,3-butanediol concentration as measured by the above HPLC analysis, the amount of 2,3-butanediol fed before the distillation as calculated from the amount of liquid fed, the amount of distillate after the distillation, and the recovery of 2,3-butanediol as calculated from the above-described GC purity.

$$\text{Distillation yield}(\%) = 100 \times \{(\text{amount of distillate after distillation}) \times (\text{GC purity})\}/\{(2,3\text{-BDO concentration before distillation}) \times (\text{amount of liquid fed before distillation})\} \quad (2)$$

Electric Conductivity

In a multi-function water quality meter (MM-60R, manufactured by DKK-TOA Corporation) equipped with an electric-conductivity cell for low electric conductivity (CT-57101C, manufactured by DKK-TOA Corporation), 16.67 wt % aqueous 2,3-butanediol composition solution was immersed at 23° C., and the electric conductivity was measured. The detected measured value was multiplied by 6 to determine the electric conductivity of 2,3-butanediol.

The results are shown in Table 4. Results obtained by distillation without addition of sodium hydroxide are also shown as Comparative Example 1.

TABLE 4

| | | Comparative Example 1 | Example 1 | Example 2 | Example 3 | Example 4 |
|---|---|---|---|---|---|---|
| Before distillation | 2,3-BDO weight [g] | 50 | 50 | 50 | 50 | 50 |
| | Amount of NaOH added [g] | 0 | 0.3 | 0.7 | 2.2 | 4.4 |

TABLE 4-continued

|  |  | Comparative Example 1 | Example 1 | Example 2 | Example 3 | Example 4 |
|---|---|---|---|---|---|---|
|  | Amount of NaOH added [mol %] | 0 | 1.5 | 3 | 10 | 20 |
|  | pH (after addition of NaOH) | 2.3 | 6 | 8 | 10 | 14 |
| After distillation | APHA | 10 | 3 | 3 | 3 | 3 |
|  | GC purity [%] | 97.8 | 99.7 | 99.9 | 99.9 | 99.9 |
|  | Distillation yield [%] | 86 | 86 | 86 | 83 | 75 |
|  | Electric conductivity [mS/m] | 78 | 18 | 3.2 | 0.6 | 0.6 |

As shown in Table 4, we found that, when the nanofiltration membrane treatment and the ion-exchange treatment were carried out, addition of the alkaline substance allowed removal of colored impurities. Further, as can be seen from the improved GC purities and the lower electric conductivities, these treatments were found to be also effective in removing other impurities.

Comparative Example 2: Nanofiltration Membrane Treatment Followed by Addition of Alkali and Distillation Similar to Example 1, a 2,3-butanediol culture liquid was prepared by the above-described method. The bacterial cells were removed by microfiltration in the same manner, and nanofiltration membrane treatment with the nanofiltration membrane SU-610 (Toray Industries, Inc.) was carried out using the membrane purification apparatus shown in FIG. 1. The resultant was subjected to thin film concentration by the method described in Example 1, and 0.7 g of sodium hydroxide, which corresponded to 3 mol %, was added to 50 g of 2,3-butanediol, followed by stirring the resulting mixture and then performing distillation under reduced pressure (5 mmHg), to obtain purified 2,3-butanediol. The results of analysis of this purified 2,3-butanediol are shown in Table 5.

Comparative Example 3: Ion-exchange Treatment Followed by Addition of Alkali and Distillation Similar to Example 1, a 2,3-butanediol culture liquid was prepared by the above-described method. The bacterial cells were removed by microfiltration in the same manner, and ion exchange was carried out by the above-described method. In this step, the amount of the ion-exchange resin was 10 times larger than that in Example 1 so that this process was suggested to be expensive. The resultant was subjected to thin film concentration by the method described in Example 1, and 0.7 g of sodium hydroxide, which corresponded to 3 mol %, was added to 50 g of 2,3-butanediol, followed by stirring the resulting mixture and then performing distillation under reduced pressure (5 mmHg), to obtain purified 2,3-butanediol. The results of analysis of this purified 2,3-butanediol are shown in Table 5.

TABLE 5

|  |  | Comparative Example 2 | Comparative Example 3 |
|---|---|---|---|
| Before distillation | 2,3-BDO weight [g] | 50 | 50 |
|  | Amount of NaOH added [g] | 0.7 | 0.7 |
|  | Amount of NaOH added [mol %] | 3 | 3 |
|  | pH (after addition of NaOH) | 9.6 | 8 |
| After distillation | APHA | 50 | 102 |
|  | GC purity [%] | 98 | 96 |
|  | Distillation yield [%] | 63 | 86 |
|  | Electric conductivity [mS/m] | 65 | 18 |

From the results shown in Table 5, it was shown that impurities such as colored components cannot be removed by nanofiltration membrane treatment or ion-exchange treatment alone even if an alkaline substance is added for distillation, and that the distillation yield is low in such a case.

Examples 5 and 6: Distillation Effect by Addition of Calcium Hydroxide and Calcium Carbonate Similar to Example 1, a 2,3-butanediol culture liquid was prepared, and microfiltration membrane treatment and nanofiltration membrane treatment were carried out followed by ion-exchange treatment and thin-film concentration, to obtain a purified 2,3-butanediol solution. Calcium hydroxide or calcium carbonate was added to 50 g of this 2,3-butanediol at 3 mol %, and the resulting mixture was sufficiently stirred. At this time, undissolved powder of calcium hydroxide or calcium carbonate was found due to their low solubility in water, but the mixture was subjected to distillation as it is. Distillation was carried out in the same manner as in Example 1. The results on the obtained purified 2,3-butanediol are shown in Table 6.

TABLE 6

|  |  | Example 5 | Example 6 |
|---|---|---|---|
| Before distillation | 2,3-BDO weight [g] | 50 | 50 |
|  | Alkaline substance | Ca(OH)2 | CaCO3 |
|  | Amount added [g] | 1.7 | 1.2 |
|  | Amount added [mol %] | 3 | 3 |
|  | pH (after addition of alkali) | 12 | 6.5 |
| After distillation | APHA | 3 | 3 |
|  | GC purity [%] | 99.9 | 99.9 |
|  | Distillation yield [%] | 83 | 85 |
|  | Electric conductivity [mS/m] | 3.0 | 4.2 |

From these results, it was shown that any of sodium hydroxide, calcium hydroxide and calcium carbonate produces a similar result as the alkaline substance.

Reference Examples 1 to 4: Purification of 2,3-Butanediol and 1,3-Propanediol Model Fermentation Liquids Preparation of 2,3-Butanediol and 1,3-Propanediol Model Fermentation Liquids Model fermentation liquids were prepared by adding 2,3-butanediol or 1,3-propanediol to the ethanol fermentation liquid described below. As an ethanol fermentation microorganism, *Escherichia coli* KO11 strain (purchased from ATCC (American Type Culture Collection)) was used. The microorganism was inoculated to 5 mL of the medium shown in Table 7, and cultured with shaking at 30° C. for 24 hours. The resultant was similarly inoculated to 50 mL of the medium shown in Table 7, and preculture was carried out under the same conditions. The resulting preculture was inoculated to 4 L of the medium shown in Table 8, and main culture was performed. The culture was carried out at a temperature of 30° C., aeration rate of 0.01 vvm and stirring rate of 400 rpm, and neutralization was carried out with potassium hydroxide and sulfuric acid such that the pH became 6.

TABLE 7

| Component | Concentration |
| --- | --- |
| Glucose | 20 g/L |
| Tryptone | 5 g/L |
| Yeast extract | 10 g/L |
| NaCl | 5 g/L |

TABLE 8

| Component | Concentration |
| --- | --- |
| Glucose | 40 g/L |
| Tryptone | 5 g/L |
| Yeast extract | 10 g/L |
| NaCl | 5 g/L |

The progress of fermentation was judged based on changes in the ethanol concentration and glucose concentration. The concentration of ethanol was measured under the following HPLC conditions. The glucose concentration was measured under the same conditions as in Example 1.
Measurement of Ethanol Concentration
Column: Shodex Sugar SH1011 (manufactured by Showa Denko K. K.)
Column temperature: 65° C.
Mobile phase: 0.05 M aqueous sulfuric acid solution, 0.6 mL/min.
Detection: RI In the this study, the ethanol fermentation reached saturation on Day 3 after the beginning of the culture. The ethanol concentration at this time was 16 g/L, and the glucose concentration was 0.9 g/L. The obtained ethanol culture liquid was filtered through a microfiltration membrane (manufactured by Toray Industries, Inc.) to remove the bacterial cells. This fermentation was repeated 8 times to obtain 32 L of an ethanol culture liquid. The ethanol culture liquid was divided into 16-L aliquots, and 480 g of 2,3-butanediol or 480 g of 1,3-propanediol was added to each aliquot to prepare a 2,3-butanediol model fermentation liquid and a 1,3-propanediol model fermentation liquid.
Nanofiltration Membrane Treatment and Ion-exchange Treatment of Model Fermentation Liquids, and Distillation Purification by Addition of Alkaline Substance The 2,3-butanediol model fermentation liquid and the 1,3-propanediol (1,3-PDO) model fermentation liquid were subjected to nanofiltration membrane treatment and ion-exchange treatment, followed by thin-film concentration by the same operations as in Example 1. To 50 g of the concentrated 2,3-butanediol solution, 0.7 g (3 mol % with respect to the amount (number of moles) of 2,3-butanediol; Reference Example 2) of sodium hydroxide was added, and, to 50 g of the concentrated 1,3-propanediol solution, 0.5 g (2 mol % with respect to the amount (number of moles) of 1,3-propanediol; Reference Example 4) of sodium hydroxide was added, followed by sufficiently stirring the resulting mixtures until the sodium hydroxide was dissolved. Each resulting solution was distilled under reduced pressure (5 mmHg), to obtain purified 2,3-butanediol and 1,3-propanediol. The degrees of coloration (APHA) of 2,3-butanediol and 1,3-propanediol after the distillation were measured by the same procedure as in Example 1. The results are shown in Table 9. Results obtained by distillation without addition of sodium hydroxide are also shown for the 2,3-butanediol solution (Reference Example 1) and the 1,3-propanediol solution (Reference Example 3).

TABLE 9

| | | Reference Example 1 | Reference Example 2 | Reference Example 3 | Reference Example 4 |
| --- | --- | --- | --- | --- | --- |
| Before distillation | 2,3-BDO weight [g] | 50 | 50 | 0 | 0 |
| | 1,3-PDO weight [g] | 0 | 0 | 50 | 50 |
| | Alkaline substance | NaOH | NaOH | NaOH | NaOH |
| | Amount added [g] | 0 | 0.7 | 0 | 0.5 |
| | Amount added [mol %] | 0 | 3 | 0 | 2 |
| | pH (after addition of alkali) | 2.5 | 8 | 4 | 8 |
| After distillation | APHA | 21 | 4 | 7 | 8 |

As shown in Table 9, it was found, based on a comparison between Reference Example 1 and Reference Example 2, that the degree of coloration of 2,3-butanediol subjected to nanofiltration membrane treatment and ion-exchange treatment is largely improved by addition of the alkaline substance and distillation. On the other hand, based on a comparison between Reference Example 3 and Reference Example 4, the increase in the degree of coloration of 1,3-propanediol subjected to nanofiltration membrane treatment and ion-exchange treatment caused by distillation without addition of an alkaline substance was smaller than that observed for 2,3-butanediol, and no improving effect on the degree of coloration was found even where the alkaline substance was added for the distillation. These results showed that, since the mechanism of coloration in the distillation step is different between 1,3-propanediol and 2,3-butanediol, a purification method suitable for each substance needs to be studied to improve the degree of coloration, and that improving the degree of coloration by addition of an alkaline substance upon the distillation is an effect specific to 2,3-butanediol.

INDUSTRIAL APPLICABILITY 2,3-Butanediol obtained by our methods can be used similarly to that derived from petroleum, as an intermediate material for pharmaceuticals and cosmetics; as a material for inks, perfumes, liquid crystals, insecticides, softening agents, explosives, plasticizers and the like; and as a material for synthetic resins.

The invention claimed is:
1. A method of producing 2,3-butanediol comprising:
    subjecting a 2,3-butanediol culture liquid produced by microbial fermentation to nanofiltration membrane treatment and ion-exchange treatment to obtain a 2,3-butanediol solution (Step A), and distillation (Step B) consisting of adding an alkaline substance then performing distillation,
        wherein pH of the 2,3-butanediol solution after adding the alkaline substance is 6 or more, and adding the alkaline substance reduces APHA of distilled 2,3-butanediol.

2. The method according to claim 1, wherein an amount of said alkaline substance added is not more than 10 mol % with respect to an amount (number of moles) of 2,3-butanediol.

3. The method according to claim 1, wherein said alkaline substance is at least one selected from the group consisting of alkali metal hydroxides, alkaline earth metal hydroxides, alkali metal carbonates, alkali metal hydrogen carbonates and alkaline earth metal carbonates.

4. The method according to claim 1, wherein said alkaline substance is at least one selected from the group consisting of sodium hydroxide, potassium hydroxide, calcium hydroxide, magnesium hydroxide, sodium carbonate and calcium carbonate.

5. The method according to claim 1, further comprising concentrating, before said Step B, the 2,3-butanediol solution (Step C).

6. The method according to claim 5, wherein said Step C is a step of filtering the 2,3-butanediol solution through a reverse osmosis membrane.

7. The method according to claim 2, wherein said alkaline substance is at least one selected from the group consisting of alkali metal hydroxides, alkaline earth metal hydroxides, alkali metal carbonates, alkali metal hydrogen carbonates and alkaline earth metal carbonates.

8. The method according to claim 2, wherein said alkaline substance is at least one selected from the group consisting of sodium hydroxide, potassium hydroxide, calcium hydroxide, magnesium hydroxide, sodium carbonate and calcium carbonate.

9. The method according to claim 2, further comprising concentrating, before said Step B, the 2,3-butanediol solution (Step C).

10. The method according to claim 3, further comprising concentrating, before said Step B, the 2,3-butanediol solution (Step C).

11. The method according to claim 4, further comprising concentrating, before said Step B, the 2,3-butanediol solution (Step C).

* * * * *

UNITED STATES PATENT AND TRADEMARK OFFICE
CERTIFICATE OF CORRECTION

PATENT NO. : 10,584,084 B2
APPLICATION NO. : 14/350366
DATED : March 10, 2020
INVENTOR(S) : Kawamura et al.

It is certified that error appears in the above-identified patent and that said Letters Patent is hereby corrected as shown below:

In the Specification

<u>In Column 16</u>
At Table 9, Column 6, Line 6, please change "2" to --3--.

Signed and Sealed this
Fifth Day of July, 2022

Katherine Kelly Vidal
*Director of the United States Patent and Trademark Office*